United States Patent
Whalen et al.

(10) Patent No.: US 7,802,466 B2
(45) Date of Patent: Sep. 28, 2010

(54) OSCILLATING SENSOR AND FLUID SAMPLE ANALYSIS USING AN OSCILLATING SENSOR

(75) Inventors: Christopher D. Whalen, Pleasant Prairie, WI (US); Klaus Wiehler, Hamburg (DE); Sven Kelling, Cambridge (GB)

(73) Assignee: Sierra Sensors GmbH, Hamburg (DE)

( * ) Notice: Subject to any disclaimer, the term of this patent is extended or adjusted under 35 U.S.C. 154(b) by 376 days.

(21) Appl. No.: 11/946,338

(22) Filed: Nov. 28, 2007

(65) Prior Publication Data
US 2009/0133470 A1 May 28, 2009

(51) Int. Cl.
G01N 29/27 (2006.01)
G01N 29/032 (2006.01)

(52) U.S. Cl. ............... 73/54.41; 73/61.49; 73/61.61; 73/61.79; 73/64.53; 73/584

(58) Field of Classification Search ............ 73/54.41, 73/61.49, 61.61, 61.75, 61.79, 64.53, 584, 73/649, 651
See application file for complete search history.

(56) References Cited

U.S. PATENT DOCUMENTS

| | | | |
|---|---|---|---|
| 5,135,852 A | 8/1992 | Ebersole et al. | |
| 5,455,475 A * | 10/1995 | Josse et al. | 310/316.01 |
| 6,037,705 A | 3/2000 | Kawabata et al. | |
| 6,196,059 B1 * | 3/2001 | Kosslinger et al. | 73/61.49 |
| 6,420,818 B1 | 7/2002 | Kishimoto et al. | |
| 6,472,798 B2 | 10/2002 | Kishimoto | |
| 6,570,299 B2 | 5/2003 | Takeshima et al. | |
| 6,911,606 B2 | 6/2005 | Suda | |

(Continued)

FOREIGN PATENT DOCUMENTS

EP 1688735 A 8/2006

(Continued)

OTHER PUBLICATIONS

Von Gunter Sauerbrey, *Verwendung von Schwingquarzen zur Wagung dunner Schichten und zur Mikrowagung*, Z. Phys. 155 (1959), p. 206-222.

(Continued)

*Primary Examiner*—David A. Rogers
(74) *Attorney, Agent, or Firm*—Boyle Fredrickson SC

(57) ABSTRACT

An assembly design for an oscillating resonator-based sensor where an oscillating crystal resonator such as a quartz crystal resonator is rigidly affixed or 'mounted' onto a solid substrate in such a fashion that the resonator can either rest flush against the substrate surface or upon a rigid mounting adhesive. Once cured, the mounting adhesive forms a liquid tight seal between the mounted resonator and the substrate such that only the sensing electrode surface will be exposed to fluids applied to the front side of the substrate. The mounted resonator assembly is designed in such a way that it can be interfaced with a fluid delivery system to form a liquid tight chamber or flow cell around the mounted resonator without incurring additional physical impact upon the mounted resonator. The assembled flow cell can in turn be used to direct multiple fluid streams to flow in a laminar manner over the sensing surface of the mounted resonator and by varying the rates of flow for the different laminar flowing fluid streams the total hydraulic pressure exerted on the surface of the mounted resonator can be held constant.

11 Claims, 2 Drawing Sheets

U.S. PATENT DOCUMENTS

| | | | |
|---|---|---|---|
| 6,960,868 B2 | 11/2005 | Ishimasa et al. | |
| 7,055,377 B2 * | 6/2006 | Paul et al. | 73/54.41 |
| 7,135,810 B2 | 11/2006 | Okajima | |
| 7,141,919 B1 | 11/2006 | Hamada et al. | |
| 2004/0016297 A1 * | 1/2004 | Paul et al. | 73/580 |
| 2006/0217893 A1 * | 9/2006 | Li et al. | 702/19 |
| 2006/0257290 A1 * | 11/2006 | Shimizu | 422/100 |
| 2007/0220970 A1 | 9/2007 | Gruber | |

FOREIGN PATENT DOCUMENTS

| | | | |
|---|---|---|---|
| JP | 2005077232 A | * | 3/2005 |
| JP | 2005331443 A | * | 12/2005 |
| JP | 2005331445 A | * | 12/2005 |
| JP | 2007078622 A | * | 3/2007 |
| JP | 2007078623 A | * | 3/2007 |
| JP | 2007085972 A | * | 4/2007 |
| WO | WO02/061396 A1 | | 3/2001 |
| WO | WO02/12873 A2 | | 2/2002 |
| WO | WO02/47246 A1 | | 6/2002 |
| WO | WO 04/001392 A | | 12/2003 |
| WO | WO2004/040268 A1 | | 5/2004 |
| WO | WO 2004/072622 A | | 8/2004 |

OTHER PUBLICATIONS

Pamela L. Konash et al., *Piozoelectric Crystals as Detectors in Liquid Chromatography*, Anal. Chem 1980, p. 1929-1931.

Uttenthaler, Erich et al., *Ultrasensitive Quartz Crystal Microbalance Sensors for Detection of M13-Phages in Liquids*, Biosensors & Bioelectronics 2001, pp. 735-743, XP002531428.

* cited by examiner

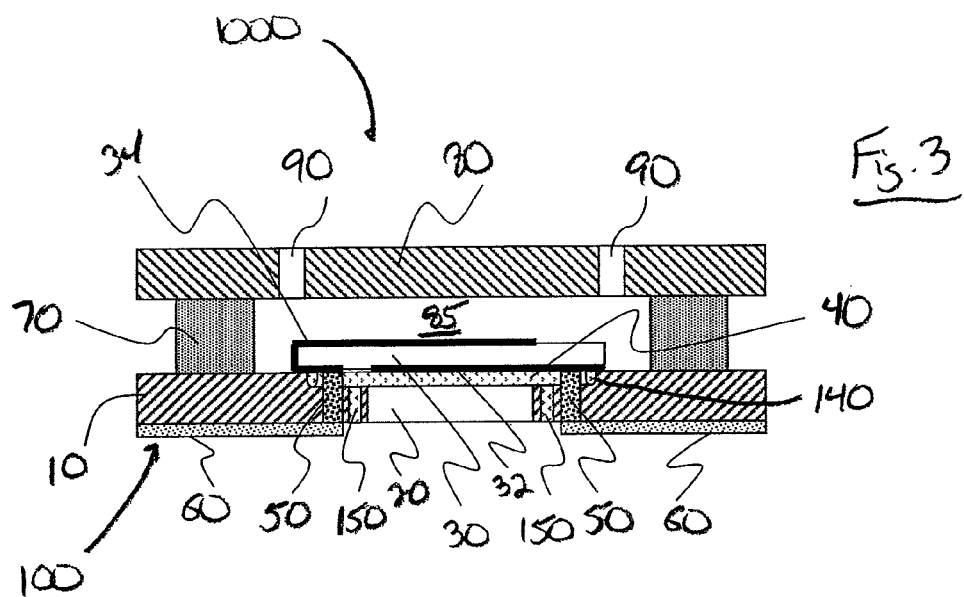
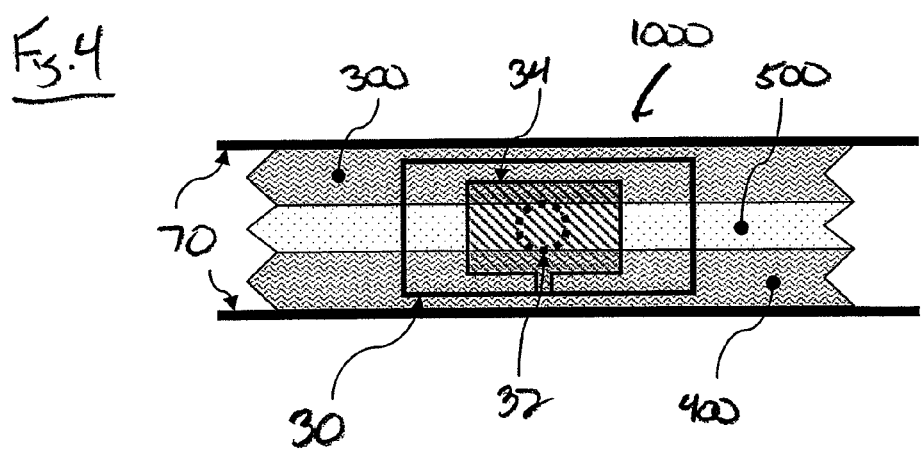

OSCILLATING SENSOR AND FLUID SAMPLE ANALYSIS USING AN OSCILLATING SENSOR

FIELD OF THE INVENTION

The invention regards a new sensor assembly and method of fluid delivery to the sensor, and more specifically pertains to a sensor assembly for fluid sample testing that includes a rigid attachment of the core sensing device to a mounting substrate to minimize and control all direct physical contact to the core sensing device of the assembly in conjunction with a unique method of test fluid delivery to control pressure fluctuations upon the core sensing device during operation.

BACKGROUND OF INVENTION

Oscillating crystal resonators can be used as very sensitive mass sensors in gas and liquid phase. It was shown by Sauerbrey (Sauerbrey, G., Z. Phys. 155 (1959), p. 206-222) that material deposited onto a resonator surface will change the resonators fundamental oscillation frequency proportional to the mass of the deposited material. Due to the extreme sensitivity of these resonators to changes in mass on their surfaces, oscillating crystal resonators can be employed to determine mass changes on a molecular level, and are often referred to as Quartz Crystal Microbalances or QCM. An oscillating crystal resonator generally consists of a thin plate of piezoelectric material, such as a quartz crystal wafer, with metal electrodes deposited on each face of the plate. Applying an electric field between the electrodes, or across the piezoelectric plate, causes a physical displacement in the piezoelectric material. Due to this "piezoelectric phenomenon" caused the by the electric current, steady oscillations of piezoelectric plates can be achieved through the application of a stable electric field in this manner. Once stable, changes in oscillation of the piezoelectric plates due to the addition or subtraction of mass from their surface can be quantified with great accuracy.

In 1980 researchers (Konash, P. L. and Bastiaans, G. J., Anal Chem. 52 (1980), p. 1929-1931), successfully utilized an oscillating crystal resonator as a sensor for measurement in the liquid phase. Over the years the use of oscillating crystal resonators as acoustic sensors in liquid phase applications have became very popular. Today there are thousands of literature publications documenting the application of oscillating quartz crystal resonators for use as liquid phase acoustic sensors. These sensors have been used to measure the presence and amount of chemical substances such as agricultural pesticides, toxins, and food additives in samples. A form of quartz sensor called a biosensor has been used to measure the presence and interactions of proteins, such as antibodies and hormones, nucleic acids, as well as pharmaceutical drugs, in liquid samples ranging from bodily fluids to organic solvents.

When operating an oscillating crystal resonators as a liquid phase sensor it is a requirement that the liquid sample interact with only one of the electrode coated surfaces on the resonator. The reasons for this are two-fold: 1) to eliminate electrical short-circuits between the electrodes of the resonator, and 2) to minimize loss of the resonator Q-factor (ratio of stored energy to dissipated energy in the piezoelectric plate) due to the liquids viscosity. To overcome the problem of creating a short-circuit between the electrodes the resonator mount design must isolate the back (driving/non-sensing) electrode from the front (sensing) electrode such that only the sensing electrode is exposed to the liquid under test. The viscosity of liquids can significantly dampen or even completely stop the oscillation of a crystal resonator. The higher the viscous load on the resonator the lower its sensitivity to changes in mass on the sensing surface. Thus, to minimize this dampening, it is preferable to expose only that part of the resonator required to perform the measurement to the liquid test sample, which again is the sensing electrode surface.

The earliest and most commonly used method for ensuring only one electrode of an oscillating crystal resonator came into contact with the liquid test sample was to sandwich, or "mount", the resonator between a pair of rubber O-rings or gaskets. The O-ring or gasket on the sensing surface of the resonator was then interfaced with a well or cell such that the sample solution can be applied to that surface without being exposed to the other parts of the resonator. An example of this double O-ring resonator mounting configuration is disclosed in U.S. Pat. No. 5,135,852. As noted by the patent's author, a problem of this resonator mounting configuration is that the O-rings or gaskets exert fluctuating and non-reproducible pressure on the oscillating resonator, which directly impacts the sensitivity of the resonator. More specifically the author stated: in this sensor structure, the seals are placed at the edge of the sensor where the interference with its oscillations is minimal. However, this setup has the following drawbacks: 1) sensor response is strongly influenced by mounting pressure of the sample fluid within the cell, and this pressure adjustment is not readily reproducible; 2) during assembly, the quartz plate is handled directly resulting in the risk of damaging the fragile quartz plate; and 3) even when fixed firmly between the O-rings, distortions due to pressure fluctuations in the tested liquid, and expansion or contractions of the plate due to thermal changes will stress the sensor plate and cause friction between the sensor and the O-ring which in turn will result in decreased Q-factor and unsteady oscillations, i.e. noise sensor response.

This description highlights one of the basic problems in the use of oscillating crystal resonators in liquid-based applications. To be effectively employed as a liquid phase biosensor, the oscillating crystal resonator needs to be physically interfaced with liquid delivery unit so that only the sensing surface comes in contact with the liquid sample. However, any and all physical contact with the resonator, i.e., from the sample fluid, the mounting structure, e.g., the O-rings, etc., dampens its oscillation freedom and thus lowers it sensitivity and overall functionality. Similar to the example discussed above, the vast majority of resonator mounting designs to date have employed the use of elastic mounting seals or elastic adhesives to hold the resonator in place and create the liquid tight seal for the test sample chamber. The argument for the continued use of flexible mounting materials is the belief that the elasticity of the seal or adhesive will minimize its dampening of the resonator oscillation. However, while this elasticity in the mounting material may minimize dampening, it clearly has an impact on reproducibility between individual measurements on a single resonator and for measurements between different resonators.

To reduce the amount of stress on the mounted resonator, reduce the signal noise, and to improve reproducibility, various assemblies have subsequently been developed which use only one flexible O-ring or gasket and secure the resonator by pressing it against a solid mount, such as for example those sensor structures disclosed in PCT Application Nos. WO/2004/040268, WO/2002/061396, and WO/2002/012873. In all of these designs, the sensing (front) surface of the resonator is in physical contact with parts, solid or flexible, of the mounting assembly. However, because the resonator oscillations propagate out to the edge of the piezoelectric plate (even if the coated electrode does not reach to the edge of the plate), any component making physical contact with the sensing surface will impact the resonator response. Also, even slight distortions of the resonator from mechanical or thermal variations of the mounting assembly will result in noise added to the sensor response. As a result, none of the designs disclosed in the applications facilitates the construction of a reproducible sensor assembly.

More recently, another form of resonator mount designed to reduce sensor noise was disclosed in PCT Application No. WO/2002/047246. In contrast to the prior art sensor designs, in this design the resonator is placed with its non-sensing surface on a solid support surface and fixed to the surface with a flexible adhesive applied only along the edge of the resonator plate. Because the resonator is not exposed to direct and variable physical pressure from clamping, and the sensing electrode is not in contact with any mounting components, a significant noise reduction for liquid sensing applications is achieved, while at the same time the sensing electrode is isolated from the driving electrode, thereby preventing a short circuit across the resonator plate. However, this improved design still suffers from a number of problems that have been discussed in literature publications released following the patent filing. In particular, in practice it is very difficult to uniformly apply flexible adhesive around the edge of the very thin resonator plates (~100 um) without depositing some amount of adhesive onto the sensing surface. It is also known that the resonator oscillations will reflect from the secured edge of the resonator plate, and thus the adhesive placed around the edge of the plate will still have an impact on the resonator response. Furthermore, while it is not physically pressed against the mounting substrate, the entire non-sensing surface of the resonator is in physical contact with the mounting substrate. Thus, even slight imperfections on the mounting surface will result in irregular stress on the resonator and noise in the sensor response.

Another problem with the use of oscillating crystal resonators in liquid based applications is the signal noise and response reproducibility issues arising from changes in hydraulic pressure on the resonator surface(s) during sample analysis. A primary requirement for the use of mounted oscillating crystal resonators in liquid based applications is the ability to expose sample-containing liquids to the sensing surface of the resonator as discrete volumes or plugs within a continuously flowing stream of a sample-less liquid. In a wide variety of applications, it is highly beneficial for the resonator sensing surface to be exposed to a liquid solution identical to that of the sample but without the sample before and after the sample solution is applied to the resonator sensing surface. It is also highly advantageous in a wide variety of applications that the exchanges from non-sample solution, to sample containing solution, and back to non-sample solution happen as instantaneously as possible. The processes involved with executing the additions and exchanges of sample and non-sample solutions to the sensing surface of the resonator result in pressure changes on the resonator surface(s), often resulting in non-reproducible stress on the resonators and dampening of the crystal oscillations. These stresses and dampening events can greatly diminish the sensitivity and reproducibility of the resonators as mass measurement sensors.

One approach to dealing with this problem has been to apply a counter-acting pressure on the backside of the resonator (driving electrode surface) to minimize irregular stress, deviations, and fluctuations on the sensing surface of the resonator. A problem with this type of solution comes from the design constraints of applying pressure on the backside of the mounted resonator due to the presence of the electrodes and the detection electronics connected to those electrodes. Also the intrinsic dampening of the resonator oscillations from exerting pressure on both faces of the resonator, and the difficulty in accurately matching the counter pressure on the driving electrode surface to the pressure being exerted on the sensing surface by the sample fluid or solution, make this practice highly impractical.

Thus, while the current resonator mounting designs are functional, they are far from optimal. Often the influence from erroneous signals in the form of response dampening, random noise, and drift created by the resonator mounting process lowers the sensitivity and reproducibility of the resonator to such a degree that the technology is not feasible for the majority of desired applications as a liquid based sensor. Clearly, to advance the use of this technology there is a requirement for an improved resonator mounting design. Ideally the mounting design would affix the oscillating crystal resonator to the mounting substrate in a highly stable, highly reproducible manner, fully isolating the liquid sample exposure to only the sensing surface of the resonator, while requiring only a minimal amount of physical contact between the mounting and sample delivery assembly and the oscillating resonator surfaces.

SUMMARY OF THE INVENTION

According to one aspect of the present invention, a sensor is provided with a crystal resonator that is affixed to a substrate for the sensor with an adhesive that forms a rigid bond between the resonator and the substrate when cured. The rigid bond between the resonator and the substrate effectively causes the resonator to vibrate in a manner that is not affected by the connection of the resonator to the substrate. This rigid connection greatly enhances the reproducibility of the vibration that can be generated within the resonator by effectively isolating the resonator from the substrate. In other words, the rigid connection between the resonator and the substrate prevents any dampening of the vibrations within the resonator as a result of this connection, as opposed to prior art flexible connections between the substrate and resonator. Further, because the resonator is rigidly affixed to the substrate, during operation the resonator will not "creep" or shift position with regard to the substrate. As such, the resonator will remain in the same position throughout multiple uses of the sensor, such that the vibration characteristics of the resonator will not change, further adding to the reproducibility of the vibrations in the resonator.

According to another aspect of the present invention, the adhesive forming the rigid bond between the resonator and the substrate is present around the entire periphery of the resonator. This ensures that the vibration characteristics of the resonator are uniform across the entire resonator, to prevent any variations in these vibration characteristics of the resonator.

According to still another aspect of the invention, the resonator is mounted to a substrate of a sensor that enables the sample fluid to be injected into a stream of a control fluid already passing over the resonator. To offset the increased pressure exerted on the overall fluid stream passing over the resonator from the introduction of the sample fluid and avoid any inaccurate affects on the vibration of the resonator, the streams of the control fluid can be reduced in volume. This maintains the overall pressure of the fluid streams passing over the resonator at a constant level, such that the only effects on the vibration of the resonator are produced by the sample fluid.

Numerous other aspects, features and advantages of the present invention will be made apparent from the following detailed description taken together with the drawing figures.

BRIEF DESCRIPTION OF THE DRAWINGS

The drawing figures illustrate the best mode currently contemplated of practicing the present invention.

In the drawings:

FIG. 3 is a cross-sectional view of a second embodiment of the sensor mounting assembly of the present invention; and FIG. 4 is a top plan view of a number of laminar fluid streams flowing over a sensor mounting assembly constructed according to the present invention.

DETAILED DESCRIPTION OF THE INVENTION

Figure 1:
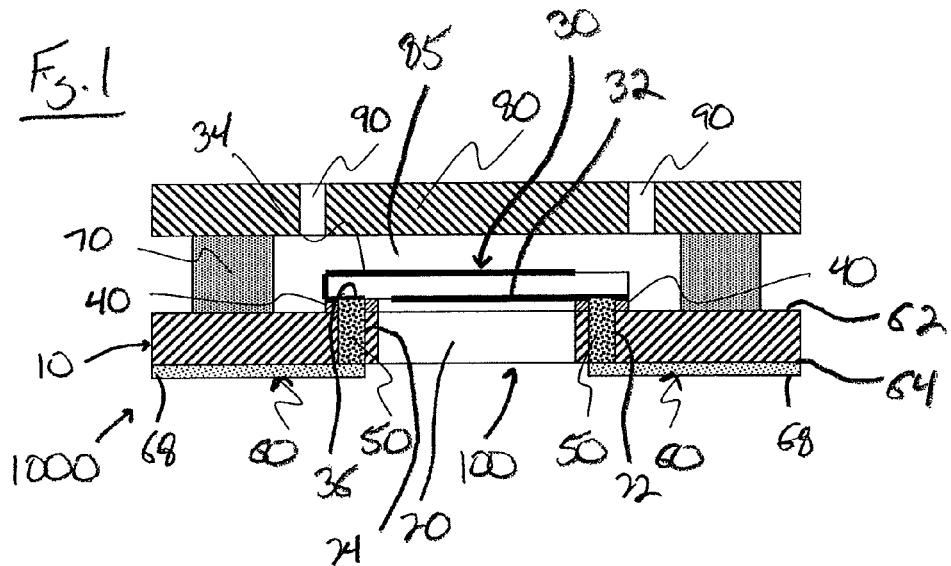
FIG. 1 is a cross-sectional view of a sensor mounting assembly constructed according to the present invention.

With reference now to the drawing figures in which like reference numerals represent like parts throughout the disclosure, a sensor assembly constructed according to the present invention is illustrated generally at 100 in FIG. 1. In one embodiment for the assembly shown in FIG. 1, the assembly 100 is a dry side sensor mounting assembly for a single sensing spot crystal resonator 30 assembled into a sample delivery flow cell 1000. The assembly 100 is formed with a substrate 10 of a fluid-impervious and non-conductive material that includes a central bore 20 and a pair of electrode contact bores 22, 24 disposed on opposite sides of the central bore 20, though the bores 22, 24 can be located in any suitable location around the bore 20. Additionally, the central bore 20 and the bores 22, 24 are shaped as desired to accommodate the particular structure of the assembly 100, and therefore can have any desired shape.

An oscillating crystal resonator 30 formed of a conventional quartz crystal material is positioned on the upper surface 62 of the substrate 10, and includes a driving electrode 32 and a sensing electrode 34 disposed on opposite sides of the resonator 30. The driving electrode 32 is positioned adjacent the upper surface 62 of the substrate 10, while the sensing electrode 34 is primarily positioned on the surface of the resonator 30 opposite the driving electrode 32. However, the sensing electrode 34 does include a wrap-around portion 36 that extends from the sensing electrode 34 around the resonator 30 onto the surface of the resonator 30 against which the driving electrode 32 is positioned. However, the wrap-around portion 36 of the sensing electrode 34 terminates at a point spaced from the driving electrode 32, and does not contact the driving electrode 32 to prevent a short circuit across the electrodes 32 and 34 on the resonator 30.

The bores 22, 24 are each filled with a conductive adhesive plug 50 that extend a short distance above the upper surface 62 of the substrate 10. The portion of these plugs 50 that extends above the upper surface 62 of the substrate 10 contacts the driving electrode 32 and the wrap-around portion 36 of the sensing electrode 34, respectively. Opposite the electrodes 32 and 34, the plugs 50 are each operably connected with one of a pair of conductive tracks 60 formed on the lower surface 64 of the substrate 10. The conductive tracks 60 formed on the lower surface 64 of the substrate 10 can be formed in any conventional manner, such as by being printed on the substrate 10 with a conductive ink, and terminate at electrical contacting pads 68 at the edges of the lower surface 64 of the substrate 10, enabling the mounted resonator 30 and the electrodes 32, 34 thereon to be easily interfaced with corresponding detection electronics systems, as are known in the art.

When positioned on the substrate 10, the driving or non-sensing electrode 32 of the resonator 30 faces the mounting substrate 10, and is positioned directly over the bore 20 such that the majority of the driving electrode 32 is not physically contacting the mounting substrate 10. The resonator 30 is also positioned onto the mounting substrate 10 such that only the terminal end of the end wrap-around portion 36 of the electrode 34 is in contact with the substrate 10. For each electrode 32 and 34, the only actual part of the electrodes 32 and 34 that is in direct contact with the substrate 10 are those portions in contact with the conductive adhesive plugs 50 and a rigid adhesive 40, to be described. For other embodiments for mounting resonators 30 possessing multiple sensing spots, and thus multiple driving electrodes 32 and/or sensing electrodes 34, the mounting substrate 10 can include multiple bores 20 for the driving electrodes 32, and multiple bores 22 and 24 for accommodating a number of conductive adhesive plugs 50, with one bore 22, 24 and corresponding plug 50 for each driving electrode 32 and sensing electrode 34. Furthermore, the bores 20-24 will be of a size such that the majority of each of the driving electrodes 32 and sensing electrodes 34 do not physically contact the substrate 10 when the resonator 30 is mounted thereto.

The resonator 30 with electrodes 32 and 34 is mounted, or affixed, onto the substrate 10 such that the electrodes 32 and 34 are disposed in contact with the plugs 50 using a very low viscosity, non-conductive, rigid bond-forming, and solvent resistant adhesive 40. One example of an adhesive that is suitable for use as the adhesive 40 is the adhesive sold under the trade name Loctite 3491, by Henkel of Düisseldorf, Germany. In one method of mounting the resonator 30 to the substrate 10, a small amount of adhesive 40 is deposited onto the upper surface 62 immediately around the driving electrode bores 20, 22, and 24 in the substrate 10. The resonator 30 is placed onto the substrate 10 with the driving electrode 32 facing the substrate 10 and in such a manner that the adhesive 40 remains only in the areas between the resonator 30 and the upper surface 62 of the substrate 10. The low viscosity of the adhesive 40 facilitates capillary distribution of the adhesive 40 to form a uniform thin film over the entire area of the upper surface 62 of the substrate 10 between the substrate 10 and resonator 30. The very small volume of adhesive 40, in part due to the particular properties of the adhesive 40, will not spread across the resonator 30 in areas where the substrate 10 has bores 20, 22, and 24, due to lack of capillary action. Therefore, the adhesive 40 does not cover any of the adjacent surface area of the driving electrode 32 or the wrap-around portion 36 of the sensing electrode 34 of the resonator 30 disposed across the central bore 20, or the electrode bores 22, 24 in the substrate 10. This distribution of the adhesive 40 between the resonator 30 and the mounting substrate 10 forms a rigid and liquid-tight seal around the central bore 20 in the substrate 10, and around all of the electrode bores 22, 24 also formed in the substrate 10, which are disposed preferably immediately adjacent the central bore 20. When cured in a suitable manner, such as by heat, UV light or over time, the adhesive 40 creates a rigid permanent seal mounting the resonator 30 to the substrate 10 while minimizing any physical contact of the adhesive 40 or the substrate 10 with the driving electrode 32 and sensing electrode 34 on the resonator 30. With this construction, the resonator 30 is rigidly secured to the substrate 10 in a manner that prevents the fluid being sensed by the sensing electrode 34 from also coming into contact with the driving electrode 32 and creating a short between the electrodes 32 and 34. Further, because the resonator 30 is mounted to the substrate 10 in rigid manner that minimizes the contact of the resonator 30 and the electrodes 32 and 34 with the substrate 10, the assembly 100 simultaneously isolates, to the extent possible, the electrodes 32 and 34 from the substrate 10, and provides a stable attachment of the resonator 30 to the substrate 10 to maintain the vibration properties of the resonator 30 constant.

When mounted in this manner using the adhesive 40, the electrodes 32 and 34 of the resonator 30 are also connected to the conductive tracks 60 on the lower surface 64 of the substrate 10 by the plugs of conductive adhesive 50 subsequently formed in the electrode bores 22, 24 present in the substrate 10. The conductive adhesive, such as the adhesive sold under the trade name Silver Conductive Paint by RS Components Ltd of Auckland, NZ, is applied into the bores 22 and 24 after attachment of the resonator 30m to the substrate 10 to form the plugs 50 in a manner such that that, when fully formed, each plug 50 contacts one of the resonator electrodes 32 and 34 at one end through the open areas in the mounting adhesive 40 remaining above the bores 22, 24 in the substrate 10, and the conductive tracks 60 on the formed on the lower surface 64 of the substrate 10 opposite the electrodes 32, 34 at the opposite end.

In order to form the assembly 100 into a flow cell 1000 for delivery of sample fluids to the resonator 30 for analysis, the assembly 100 has a liquid sealing gasket 70 of a known height positioned on the substrate 10 around the resonator 30. The gasket 70 can be formed of any desired material, with a fluid-impervious solvent resistant rubber or silicone being especially preferred. Subsequently, a fluid delivery block 80 formed of a material similar to that used for the substrate 10 is secured to the gasket 70 opposite the substrate 10. The fluid delivery block 80 is affixed to the gasket 70 in any suitable fluid-tight manner to enclose and define the interior 85 of the flow cell 1000, and is shaped to have a number of fluid delivery ports 90 formed therein. The shape and height of the sealing gasket 70 determines the shape and total volume of the flow cell 1000, and is selected such that neither the sealing gasket 70 nor the fluid delivery block 80 will make physical contact with the mounted resonator 30 when the gasket 70 and fluid delivery block 80 are engaged with the substrate 10, such as by clamping the gasket 70 and block 80 to the substrate 10. In addition, the positions of the fluid delivery ports 90 on the fluid delivery block 80 are disposed relative to the shape of the sealing gasket 70 such that fluid samples entering the cell must pass over the sensing electrode 34 on the mounted resonator 30 prior to exiting the cell 1000. The number of ports 90 formed in the block 80 can be selected as desired based on the number of fluid sources that are to be introduced into the flow cell 1000. Also, the positions of the ports 90 can be located such that the fluid streams introduced into the flow cell can be removed from the cell 1000 after passing over the resonator 30.

Figure 2:
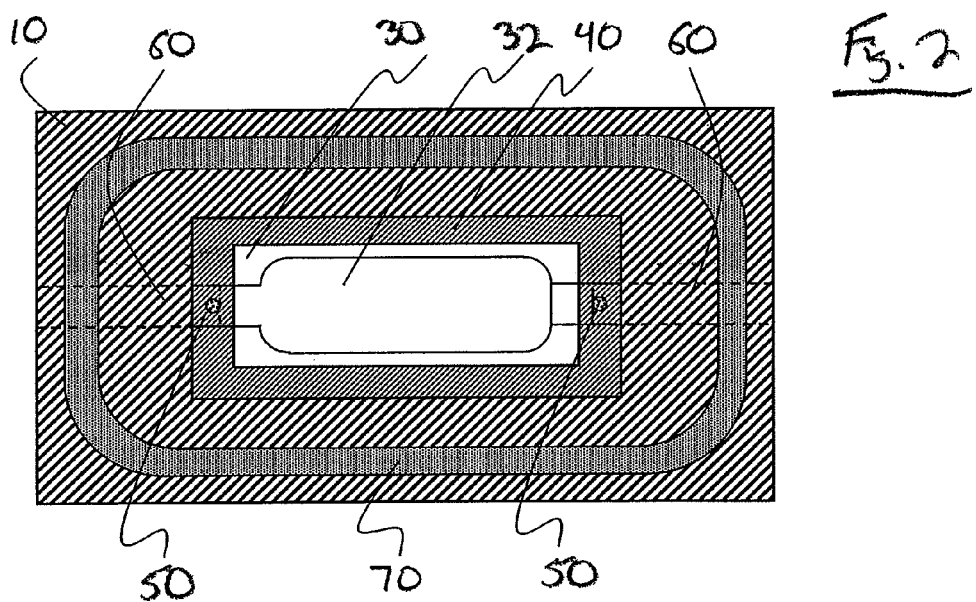
FIG. 2 is a top plan view of the assembly of FIG. 1.

Referring now to FIG. 2, in an alternative embodiment of the construction of the driving electrode 32 on the resonator 30, the driving electrode 32 is designed so that only the 'neck' of the driving electrode 32 on the resonator 30 physically contacts the mounting substrate 10. In this configuration, the amount of the surface of the driving electrode 32 that contacts the substrate 10 via the adhesive 40 and the plug 50 is further minimized Looking now at FIG. 3, another alternative construction for the assembly 100' is illustrated that utilizes an adhesive channel 140. This assembly 100 is very similar to the assembly 100' illustrated in FIG. 1, with the key difference being the fact that the mounting adhesive 40 that bonds the resonator 30 to the mounting substrate 10 is contained within an etched channel 140 cut into the upper surface 62 of the of the substrate 10. By confining the mounting adhesive 40 to the etched channel 140 when the resonator 30 is mounted, the portion of the driving electrode 32 on the resonator 30 that is to be connected to the plug 50 partially rests flush against the upper surface 62 of the mounting substrate 10. The use of the adhesive channel 140 ensures that this portion of the driving electrode 32 contacts the upper surface 62 of the mounting substrate 10 in a uniform and rigid manner, which results in more uniform and reproducible pressure on the driving electrode 32. The channel 140 also helps to ensure the entire surface area of sensing electrode surface 34 is an equidistant height from the upper surface 62 of the mounting substrate 10. Thus, when the mounted resonator 30 is interfaced with a fluid delivery block 80 and gasket 70 to form a flow cell 1000, the space between the fluid delivery block 80 and the entire exposed surface of the sensing electrode 34 is uniform.

To mount the resonator 30 onto a mounting substrate 10 possessing an adhesive channel 140, an amount of the adhesive 40 sufficient to contact those parts of the resonator 30 that are to be located directly over the channel 140 is deposited into the channel 140. The resonator 30, with driving electrode 32 facing the mounting substrate 10, is placed onto the substrate 10 so that the majority of the driving electrode 32 lies within or over the central bore 20 which is circumscribed by the channel 140, and the driving and sensing electrodes 32 and 34 are located in alignment with the conductive adhesive bores 22 and 24 and also circumscribed by the channel 140. Any excess adhesive 40 present in the channel 140 during the mounting process will escape through a number of adhesive exhaust holes 150 formed in the substrate 10 below the channel 140. Alternatively, the resonator 30 can first be properly positioned onto the mounting substrate 10 over and/or partially within the channel 140, and then mounting adhesive 40 can be injected into the adhesive channel 140 through one or more of the adhesive exhaust holes 150 with any excess adhesive 40 escaping through the other exhaust holes 150. As in previous embodiments, when the adhesive 40 cures, it contracts, slightly pulling the resonator 30 into tight engagement against the mounting substrate 10 and forms a rigid, liquid tight bond between the resonator 30 and substrate 10. However, the width of the adhesive channel 140 in relation to the size of the resonator 30 is in a ratio that is small enough not to cause the resonator 30 to bend as the curing adhesive 40 contracts. After the adhesive 40 has sufficiently cured, the conductive adhesive plugs 50 can then be formed within the bores 22 and 24 to connect the electrodes 32 and 34 on the resonator 30 to the conductive tracks 60 on the lower surface 64 of the substrate 10.

After the assembly 100 and the flow cell 1000 have been constructed in the above manner, it is then possible to pass a fluid stream through the flow cell 1000 in order to allow variations in the vibrations of the resonator 30 caused by materials in the fluid attaching to the resonator 30 to be detected, and thus obtain information concerning the components of the fluid sample flowing over the resonator 30. To do so, it is necessary to pass the fluid sample to be analyzed directly over the resonator 30 when it is injected into the flow cell 1000. It is known that when two or more independent streams of fluid flowing under conditions of laminar flow, i.e., a low Reynolds number for the flow, are in direct contact with each other and flow in the same direction, i.e. flow parallel to one another, there will be no mixing of the fluids other than by diffusion. Also, by varying the rates of flow of the different fluid streams in relation to each other, the size and position of the streams can be altered, as disclosed in Biosensors and Bioelectronics Vol. 13 No. 3-4, pages 47-438, 1998, such that the fluid streams can be moved within the space through which they are flowing by changing the relative flow rates. It is also known that oscillating crystal resonators, such as quartz crystal resonators, possess an area of higher detection sensitivity based on the dimensions of the driving electrode of the resonator in relation to the sensing electrode, as discussed in Ward and Delawski, *Anal. Chem.* 1991, 63, 886-890. Thus, focusing the flow of a sample fluid stream over this detection 'sweet spot' provides a benefit in the use of oscillating crystal resonators 30 as sensors by minimizing the amount of sample consumption needed to achieve the most efficient level of detection sensitivity.

Referring now to FIG. 4, a close up section of the previous describe flow cell embodiments where only a flow cell area 1000 is illustrated that includes the sensing electrode 34 of a substrate mounted resonator 30 in any one of the above-described manners, and a fluid delivery block 80 disposed above the resonator 30 and engaged with the substrate by a gasket 70. In FIG. 4, the fluid delivery block 80 is not shown as in the previous embodiments, but it is implied that the various fluid streams 300, 400 and 500 are introduced into the flow cell 1000 through the respective fluid delivery ports 90 located in the delivery block 80. In FIG. 4 the substrate onto which the resonator 30 is mounted is not shown in detail as in previous embodiment, but is implied to constitute the entire surface area beneath the resonator 30 and within the gasket 70 boundaries. The two guide fluid streams 300 and 400 are continuously directed into the flow cell 1000 prior to the introduction of any sample fluid stream 500. These guide fluid streams 300 and 400 also provide a baseline hydrostatic pressure exerted onto the sensing electrode 34 of the resonator 10. When the sample fluid stream 500 is introduced into the flow cell 1000 through one of the fluid delivery ports 90, the guide fluid streams 300 and 400 are able to control the position and width of the sample or reagent fluid stream 500 through the flow cell 1000 via the process of hydrodynamic focusing described previously. By controlling the flow rate of the guide fluid streams 300 and 400 relative to that of the sample or reagent fluid stream 500, it is possible to direct or position the sample or reagent fluid stream 500 over the portion of the sensing electrode 3 of the resonator 30 that is positioned directly over the driving electrode 32, located on the back side of the resonator 30) or the 'sweet spot' of detection defined by the relative positions of the electrodes 32 and 34 located on either face of the resonator 30.

In addition, as with any enclosed chamber, the addition or removal of fluid from that chamber will change the hydrostatic pressure on all walls of the chamber. In the above described assembly where the flow cell 1000 is created over a substrate to which the resonator 30 is mounted in any of the previously described manners, the addition or removal of one or more of the fluid streams 300, 400 or 500 from the enclosed flow cell 1000 will change the hydrostatic pressure on the surface of the resonator 30, and thus alter its detection response. Therefore, to maintain a constant level of hydrostatic pressure on the mounted resonator 30 within an enclosed flow cell 1000 during the delivery or removal of sample or reagent fluid streams 300, 400 and/or 500 to the sensing surface 34 of the resonator 30, when the flow cell 1000 constructed according to the present invention is operated to inject a sample fluid stream 500 into the cell 1000, the flow rates of the constantly flowing guide fluid streams 300 and 400 are altered to compensate for this pressure change. More particularly, during normal operation of the flow cell 1000, the guide fluid streams 300 and 400 are introduced through one or more of the fluid delivery ports 90 to continuously flow through the flow cell 1000 defined by the mounting substrate, the fluid delivery block 80 and the liquid sealing gasket 70. These guide fluid streams 300 and 400 create a specific and constant pressure upon the sensing electrode 34 of the mounted resonator 30 within the flow cell 1000 based on their rate of flow. When introducing a sample fluid stream 500 into the flow cell 1000 through a separate fluid delivery port 90 for analysis, the flow rate of the guide fluid streams 300 and 400 already flowing in the cell 1000 are lowered by a rate corresponding or equivalent to the rate of flow of the newly introduced fluid stream 500. This adjustment is in addition to the adjustment of the flow rates of the guide fluid streams 300 and 400 relative to the flow of the sample fluid stream 500 to direct the sample fluid stream 500 over the sensing electrode 34 in such a manor that it is focused on a path equivalent to the width of the driving electrode 32 on the backside of the resonator 10. When the flow of the sample fluid stream 500 is stopped, the flow rates of the guide fluid streams 300 and 400 are increased to compensate for the loss of fluid entering the cell 1000, and maintain the constant pressure level on the sensing electrode 3 of the resonator 30. In this manner, when all of the various fluid streams 300, 400 and 500 are generally equal in their composition or density of the carrier fluid from which they are formed, the hydrostatic static pressure within the cell 1000 is held constant to achieve a consistent response from the resonator 30 when analyzing a sample fluid.

Various alternatives are contemplated as being within the scope of the following claims particularly pointing out and distinctly claiming the subject matter regarded as the invention.

We claim:

1. A sensor comprising:
   a) a substrate including at least one bore extending therethrough; and
   b) an oscillating sensing device rigidly mounted to one surface of the substrate over the bore, the sensing device including a first electrode disposed in communication with the at least one bore and a second electrode disposed on the oscillating sensing device opposite the first electrode, wherein the oscillating sensing device is affixed to the substrate by an adhesive positioned around the periphery of the at least one bore, and wherein the adhesive is disposed within a channel formed in the substrate around the periphery of the at least one bore.

2. The sensor of claim 1 further comprising at least one adhesive exit port extending through the substrate into connection with the channel.

3. A sensor comprising:
   a) a substrate including at least one bore extending therethrough; and
   b) an oscillating sensing device rigidly mounted to one surface of the substrate over the bore, the sensing device including a first electrode disposed in communication with the at least one bore and a second electrode disposed on the oscillating device opposite the first electrode, wherein each of the first and second electrodes are operably connected to a conductor passing through the substrate and the adhesive and wherein the first electrode is disposed positioned directly over and circumscribed by the at least one bore except at the point where contacted by the conductor.

4. A flow cell for use in analyzing fluid samples, the flow cell comprising:
   a) sensor comprising a substrate including at least one bore extending therethrough and an oscillating sensing device rigidly mounted to one surface of the substrate over the bore, the sensing device including a first electrode disposed in communication with the at least one bore and a second electrode disposed on the oscillating sensing device opposite the first electrode;
b) a sealing member secured in a fluid-tight manner to the substrate around the oscillating sensing device; and
c) a flow deliver block secured to the sealing member in a fluid-tight manner opposite the substrate and including a number of fluid dispensing ports formed therein, wherein the oscillating sensing device is mounted by an adhesive flush against the surface of the substrate to completely cover the at least one bore.

5. A flow cell for use in analyzing fluid samples, the flow cell comprising:
a) sensor comprising a substrate including at least one bore extending therethrough and an oscillating sensing device rigidly mounted to one surface of the substrate over the bore, the sensing device including a first electrode disposed in communication with the at least one bore and a second electrode disposed on the oscillating sensing device opposite the first electrode;
b) a sealing member secured in a fluid-tight manner to the substrate around the oscillating sensing device; and
c) a flow deliver block secured to the sealing member in a fluid-tight manner opposite the substrate and including a number of fluid dispensing ports formed therein, wherein the sealing member and the flow delivery block do not contact the oscillating sensing device.

6. A method of assembling a sensor comprising the steps of:
a) providing an oscillating sensing device having a first electrode disposed on one side of the device and a second electrode disposed on the device opposite the first electrode; and
b) rigidly securing the oscillating device to a surface of a substrate such that the device completely covers at least one bore formed through the substrate and such that the first electrode is positioned substantially within the at least one bore, wherein the step of rigidly securing the oscillating device to the substrate comprises the steps of:
   i) applying an adhesive to one of a periphery of the oscillating sensing device or a periphery of the at least one bore in the substrate; and
   ii) pressing the oscillating sensing device and the substrate into engagement with one another.

7. The method of claim 6 further comprising the step of forming a conductor that is operably connected to one of the first electrode or the second electrode through the substrate after pressing the oscillating sensing device and the substrate into engagement with one another.

8. The method of claim 6 further comprising the steps of:
a) securing a sealing member to a fluid delivery block to define an interior within the sealing member sufficient to completely encompass the oscillating sensing mechanism; and b) engaging the sealing member with the substrate around the oscillating sensing mechanism.

9. A method for analyzing a fluid sample utilizing a flow cell including a substrate including at least one bore extending therethrough, and an oscillating sensing device rigidly mounted to one surface of the substrate over the bore, the sensing device including a first electrode disposed in communication with the at least one bore and a second electrode disposed on the oscillating sensing device opposite the first electrode and a fluid delivery block affixed to and spaced from the substrate over the oscillating sensing device by a sealing member, the method comprising the steps of:
a) introducing at least one guide fluid stream into the flow cell through the fluid delivery block to flow over the oscillating sensing device to generate a hydrostatic pressure value within the flow cell;
b) introducing at least one sample fluid stream into the flow cell through the flow delivery block at a location separate from the at least one guide fluid stream to flow over the oscillating sensing device; and
c) reducing the flow rate of the at least one guide fluid stream simultaneously with the introduction of the at least one sample fluid stream to maintain the hydrostatic pressure value within the flow cell constant.

10. The method of claim 9 wherein the step of introducing the at least one guide fluid stream comprises introducing at least two guide fluid streams into the flow cell through spaced locations in the fluid delivery block; and wherein the step of reducing the flow rate of the at least one guide fluid stream comprises varying the flow rate of at least one of the at least two guide fluid streams to shift a flow path of the at least one sample fluid stream within the flow cell simultaneously with maintaining constant the hydrostatic pressure value within the flow cell.

11. A method for analyzing a fluid sample utilizing a flow cell including a sensing device disposed within the flow cell and a fluid delivery block configured to direct multiple fluid streams into the flow cell over the sensing device, the method comprising the steps of:
a) introducing at least one guide fluid stream into the flow cell through the fluid delivery block to flow over the sensing device to generate a hydrostatic pressure value within the flow cell;
b) introducing a sample fluid stream into the flow cell through the flow delivery block at a location separate from the at least one guide fluid stream to flow over the sensing device; and
c) reducing the flow rate of the at least one guide fluid stream simultaneously with the introduction of the sample fluid stream to maintain the hydrostatic pressure value within the flow cell constant.

* * * * *